United States Patent

Hohlen

[11] Patent Number: 5,779,629
[45] Date of Patent: Jul. 14, 1998

[54] DUAL AXIS RETRACTOR

[76] Inventor: Robert D. Hohlen, 3735 W. 82nd St., Hastings, Nebr. 68901

[21] Appl. No.: 942,763

[22] Filed: Oct. 2, 1997

[51] Int. Cl.[6] .................................................. A61B 17/00
[52] U.S. Cl. ........................................................ 600/233
[58] Field of Search .................................. 600/219, 222, 600/224, 227, 231, 232, 233, 201, 235, 243, 237, 238, 242

[56] References Cited

U.S. PATENT DOCUMENTS

| Re. 34,150 | 12/1992 | Santilli et al. |
|---|---|---|
| 1,707,689 | 4/1929 | Sloan .................... 600/233 |
| 1,963,173 | 6/1934 | Morin . |
| 2,473,266 | 6/1949 | Wexler . |
| 3,038,468 | 6/1962 | Raeschle . |
| 4,627,421 | 12/1986 | Symbas et al. |
| 5,052,373 | 10/1991 | Michelson . |
| 5,067,477 | 11/1991 | Santangelo . |
| 5,400,774 | 3/1995 | Villalta et al. |
| 5,520,610 | 5/1996 | Giglio et al. ............ 600/233 |

FOREIGN PATENT DOCUMENTS

| 824754 | 2/1938 | France ................ 600/233 |
| 1069793 | 1/1984 | U.S.S.R. ............. 600/233 |

*Primary Examiner*—Jeffrey A. Smith
*Attorney, Agent, or Firm*—Zarley, McKee, Thomte, Voorhees & Sease; Mark D. Frederiksen

[57] ABSTRACT

A dual axis retractor includes a generally L-shaped frame with a base leg and an arm projecting transversely from the leg. A second arm is operably mounted to the base leg parallel to the first arm, for selective movement towards and away from the first arm. Retractor blades are mounted on the first and second arms, opposing one another, and are movable towards and away from one another upon movement of the second arm relative to the first arm. A second pair of retractor blades are mounted on a pair of linkages extending between the first and second arms. The linkages orient the second pair of blades for movement towards and away from one another along an axis orthogonal to the axis of movement of the first pair of blades. The second arm is provided with a rotatable pinion which engages a rack on the base leg to selectively move the second arm relative to the first arm, and thereby simultaneously move both pairs of retractor blades.

17 Claims, 6 Drawing Sheets

DUAL AXIS RETRACTOR

TECHNICAL FIELD

The present invention relates generally to surgical retractors, and more particularly to an improved retractor operable to retract simultaneously along two orthogonal axes.

BACKGROUND OF THE INVENTION

Heart surgery is conventionally a major invasive type of surgery requiring the ribs be spread or divided and the removing or breaking of parts of the sternum.

A minimally invasive heart surgery for the repair of heart valves may be accomplished with the use of a retractor which can simultaneously retract and maintain a hole in a chest cavity along two orthogonal axes.

Retractors are well known in the field, and conventionally retract and hold an opening along a single axis. A recent patent on a four blade medical retractor, U.S. Pat. No. 5,400,774, discloses a retractor which will retract along two independent axes, but which requires separate and independent operation of the retractor along each of the axes.

SUMMARY OF THE INVENTION

It is therefore a general object of the present invention to provide an improved dual axis retractor which will simultaneously retract along both axes.

A further object is to provide a dual axis retractor which is operable with a single force to retract uniformly along two orthogonal axes.

Still another object of the present invention is to provide an improved dual axis retractor which has adjustable retractor blades for various sizes of openings.

Yet another object is to provide a dual axis retractor which is simple to use, and economical to manufacture.

These and other objects of the present invention will be apparent to those skilled in the art.

The dual axis retractor of the present invention includes a generally L-shaped frame with a base leg and an arm projecting transversely from the leg. A second arm is operably mounted to the base leg parallel to the first arm, for selective movement towards and away from the first arm. Retractor blades are mounted on the first and second arms, opposing one another, and are movable towards and away from one another upon movement of the second arm relative to the first arm. A second pair of retractor blades are mounted on a pair of linkages extending between the first and second arms. The linkages orient the second pair of blades for movement towards and away from one another along an axis orthogonal to the axis of movement of the first pair of blades. The second arm is provided with a rotatable pinion which engages a rack on the base leg to selectively move the second arm relative to the first arm, and thereby simultaneously move both pairs of retractor blades.

DESCRIPTION OF THE PREFERRED EMBODIMENT

Figure 1:
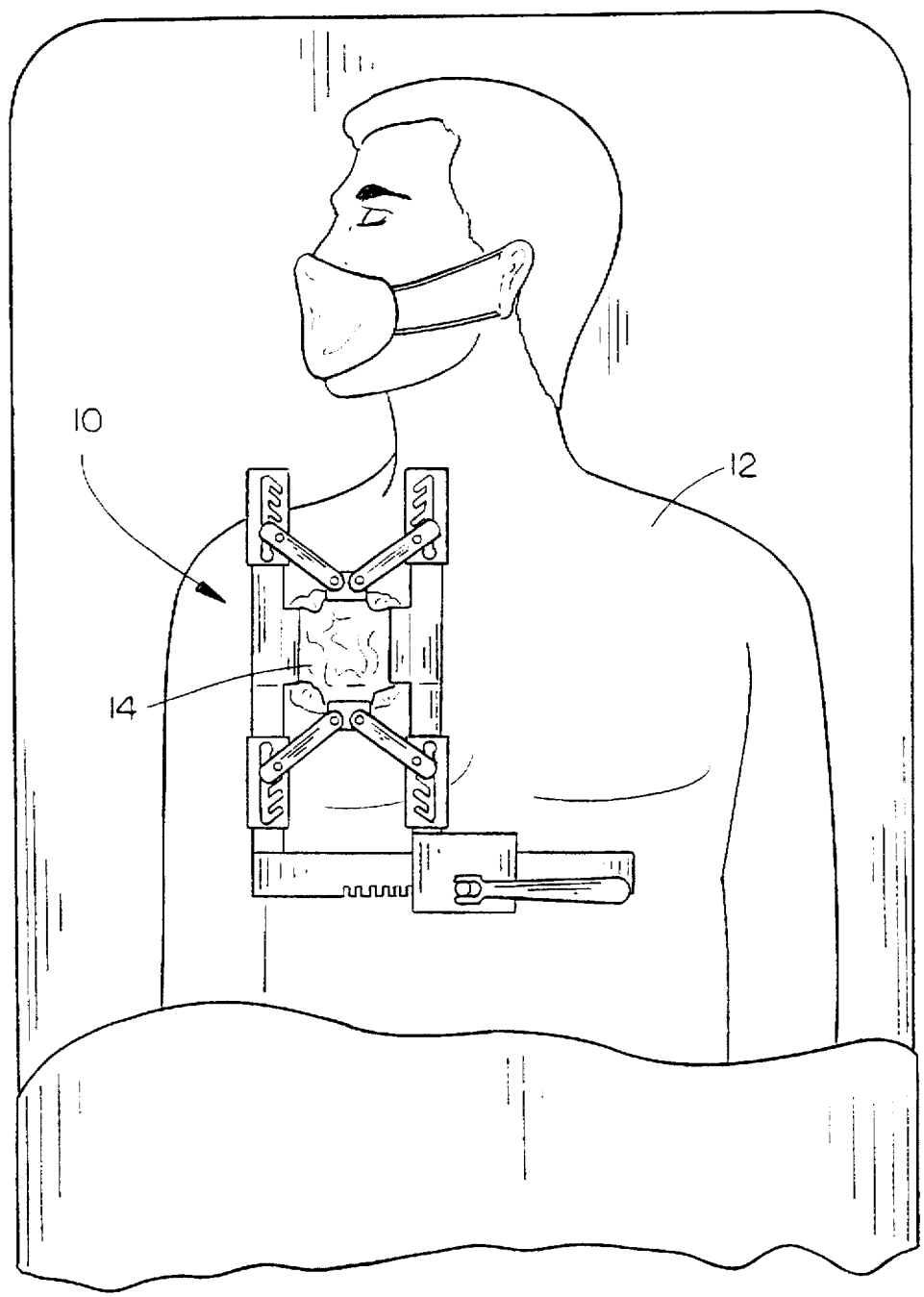
FIG. 1 is a top view of the retractor in use on a patient.

Referring now to the drawings, in which similar or corresponding parts are identified with the same reference numeral and more particularly to FIG. 1, the dual axis retractor of the present invention is designated generally at 10 and is shown in use on a patient 12 to retract and maintain an opening 14 in the patient's body.

Figure 2:
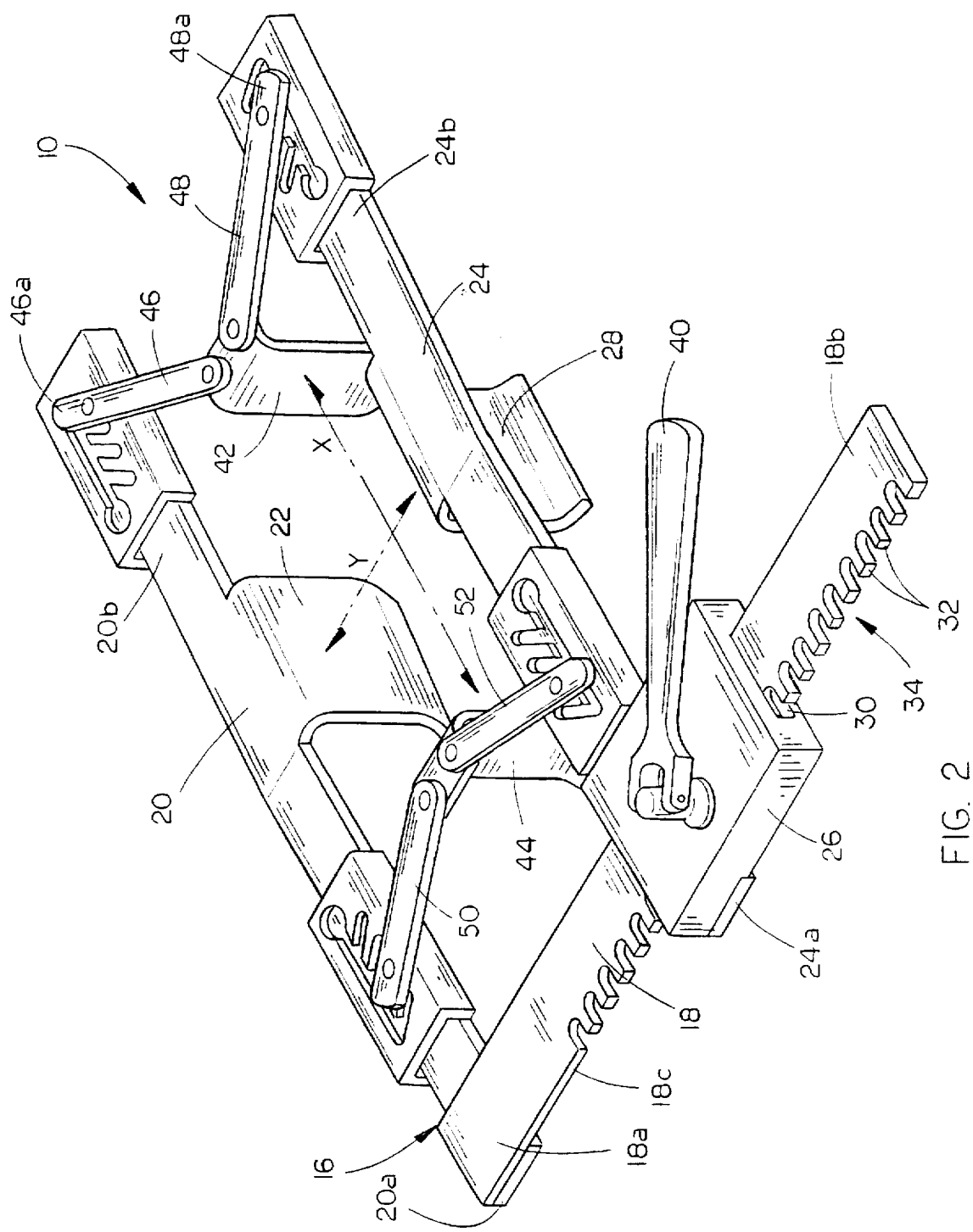
FIG. 2 is an enlarged perspective view of the retractor.
Figure 3:
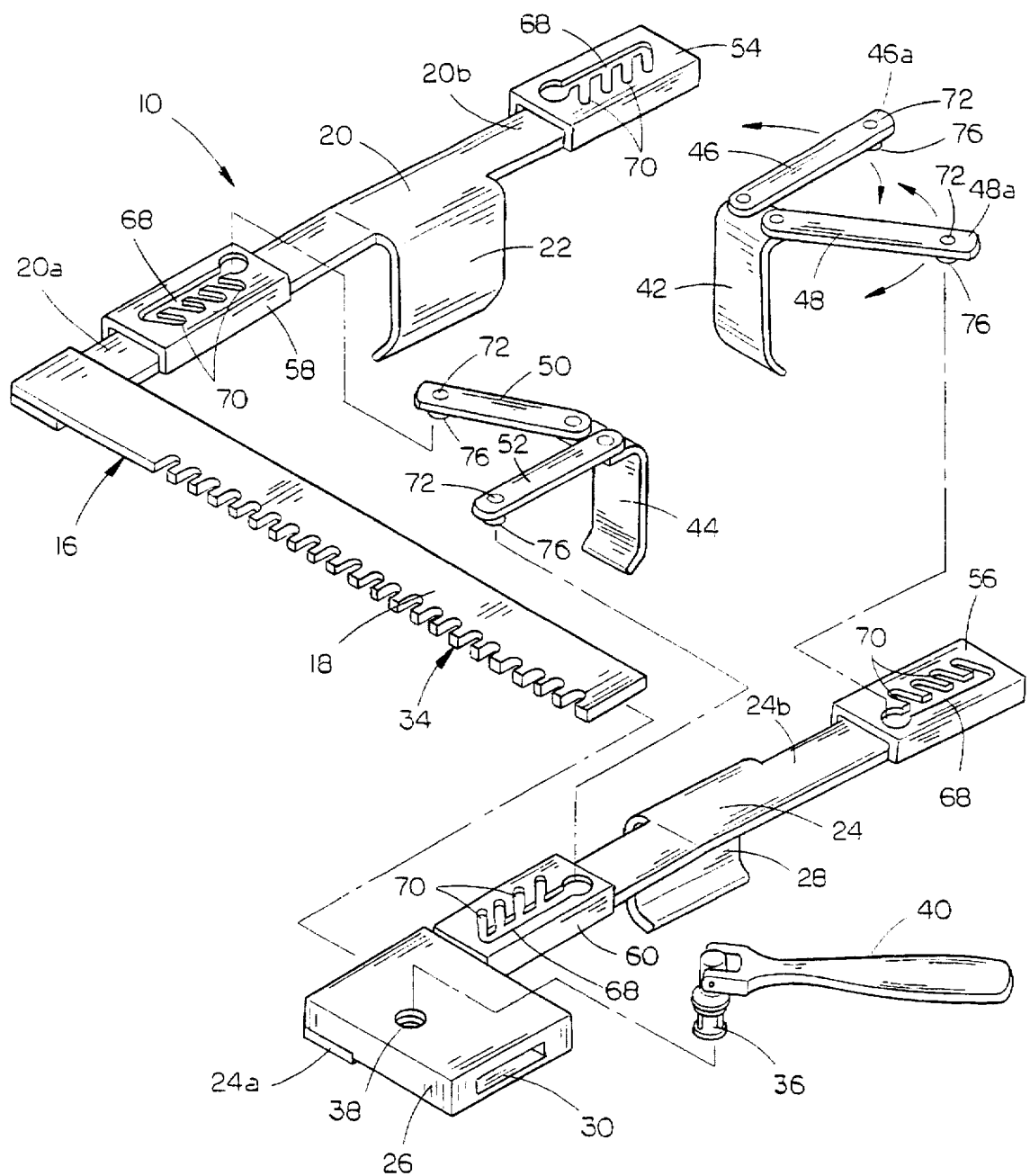
FIG. 3 is an exploded perspective view of the retractor.
Figure 6:
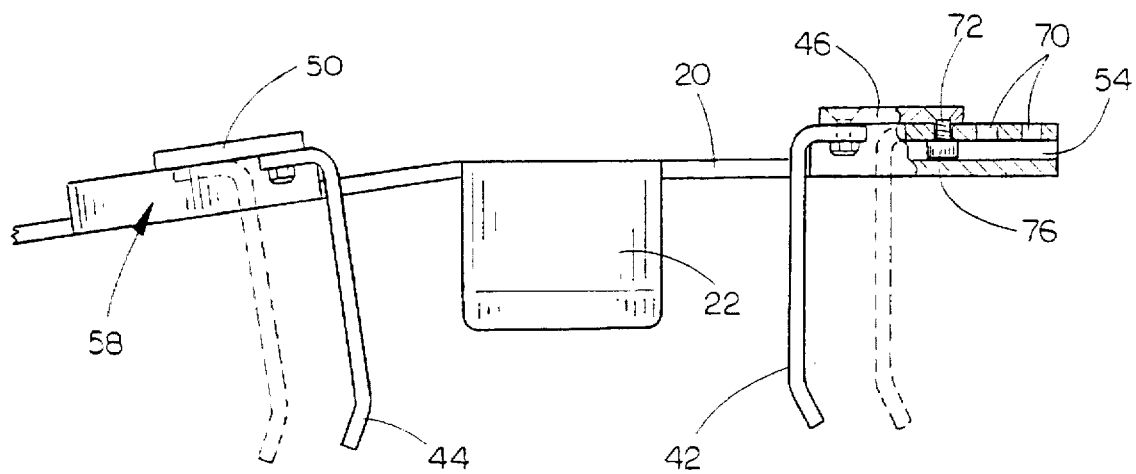
FIG. 6 is a side elevational view showing one retractor arm and the adjustable positions of two of the retractor blades.

Referring now to FIGS. 2 and 3, the retractor 10 includes a generally L-shaped frame 16 formed of a base leg 18, having forward and rearward ends 18a and 18b respectively, and a longitudinal arm 20 connected at a first end 20a to the forward end 18a of base leg 18, and projecting therefrom. Arm 20 includes a plate-like blade 22 depending intermediate the forward and rearward ends 20a and 20b, for retracting tissue in a patient. Preferably, arm 20 is curved or bent along its longitudinal axis (as shown in more detail in FIG. 6) so as to follow the general curvature of a patient's body.

A second longitudinal arm 24 is rigidly mounted at a first end 24a to a carrier housing 26. Carrier housing 26 is operably connected to the frame base leg 18 to selectively move second arm 24 forwardly and rearwardly towards and away from first arm 20, and in parallel relationship thereto. Second arm 24 includes a blade 28 located parallel and opposite blade 22 on first arm 20. Preferably, blades 22 and 28 are curved outwardly away from each other.

Carrier housing 26 has a slot 30 formed transversely therethrough, through which base leg 18 is journaled. Base leg 18 has teeth 32 formed along the length of one edge 18c thereof, forming a rack 34 for engaging a pinion 36 (shown in FIG. 3). Pinion 36 is rotatably mounted through an aperture 38 in carrier housing 26, and located to shift rack 34 forwardly and rearwardly through slot 30 when pinion 36 is rotated within aperture 38. A crank 40 is attached to pinion 36 to selectively rotate the pinion in a conventional fashion.

Thus, blades 22 and 28 on parallel longitudinal arms 20 and 24 may be moved towards and away from one another by the rotation of pinion 36 with crank 40.

A second pair of blade s 42 and 44 are connected between arms 20 and 24, and are operable to move towards or away from one another along a longitudinal axis designated as the X axis in the drawings, the X axis being generally parallel to arms 20 and 24. Blades 22 and 28 move towards and away from one another along a transverse axis, designated as a Y axis in the drawings.

Blade 42 has a pair of links 46 and 48 pivotally connected at one end to the upper end of the blade 42. The distal ends 46a and 48a of links 46 and 48 are pivotally connected to ends 20b and 24b of arms 20 and 24, respectively.

Similarly, blade 44 is pivotally connected to the opposing ends 20a and 24a of arms 20 and 24 via links 50 and 52.

Figure 4:
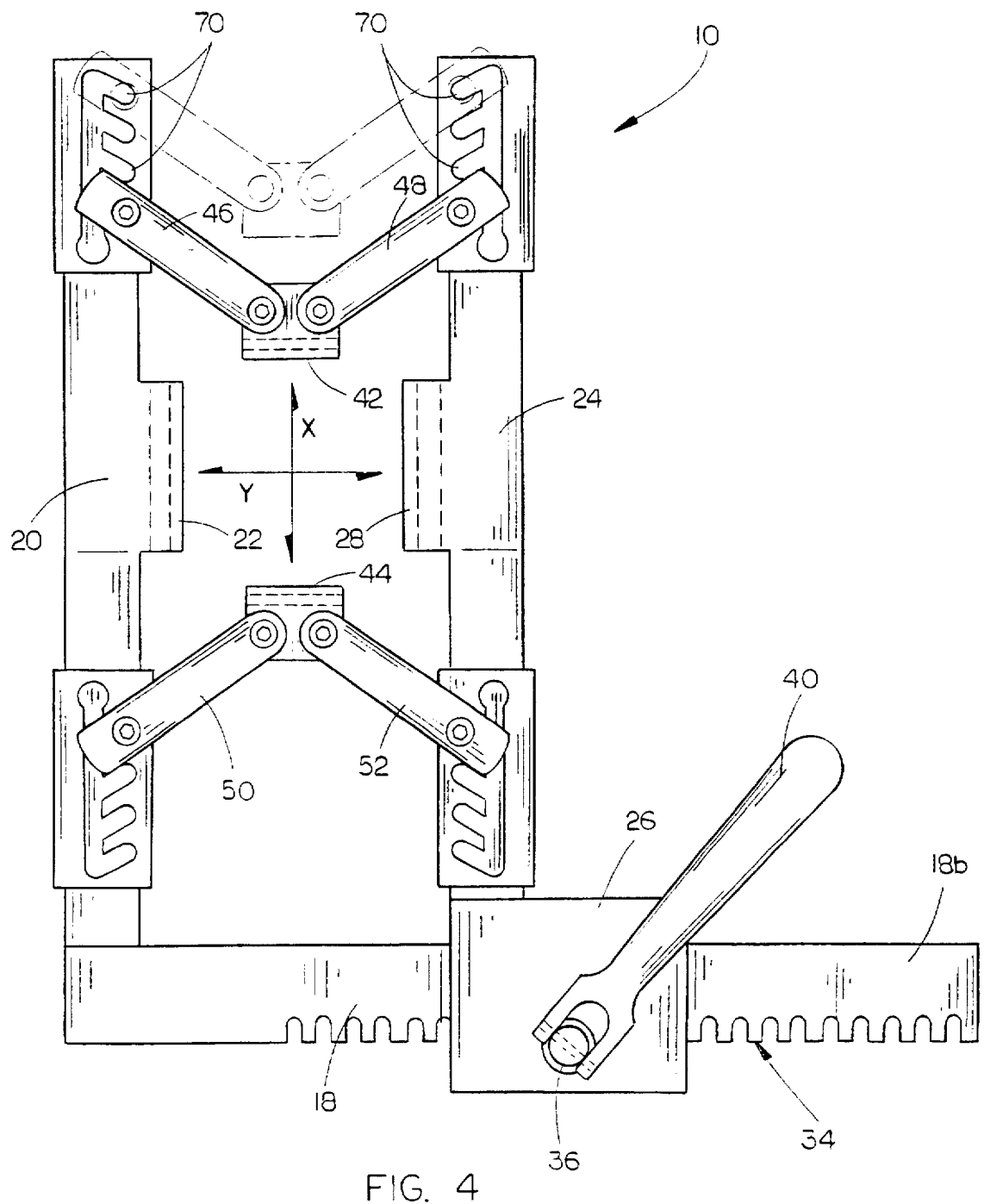
FIG. 4 is a top plan view of the retractor with broken lines indicating an alternate position for one retractor blade.
Figure 5:
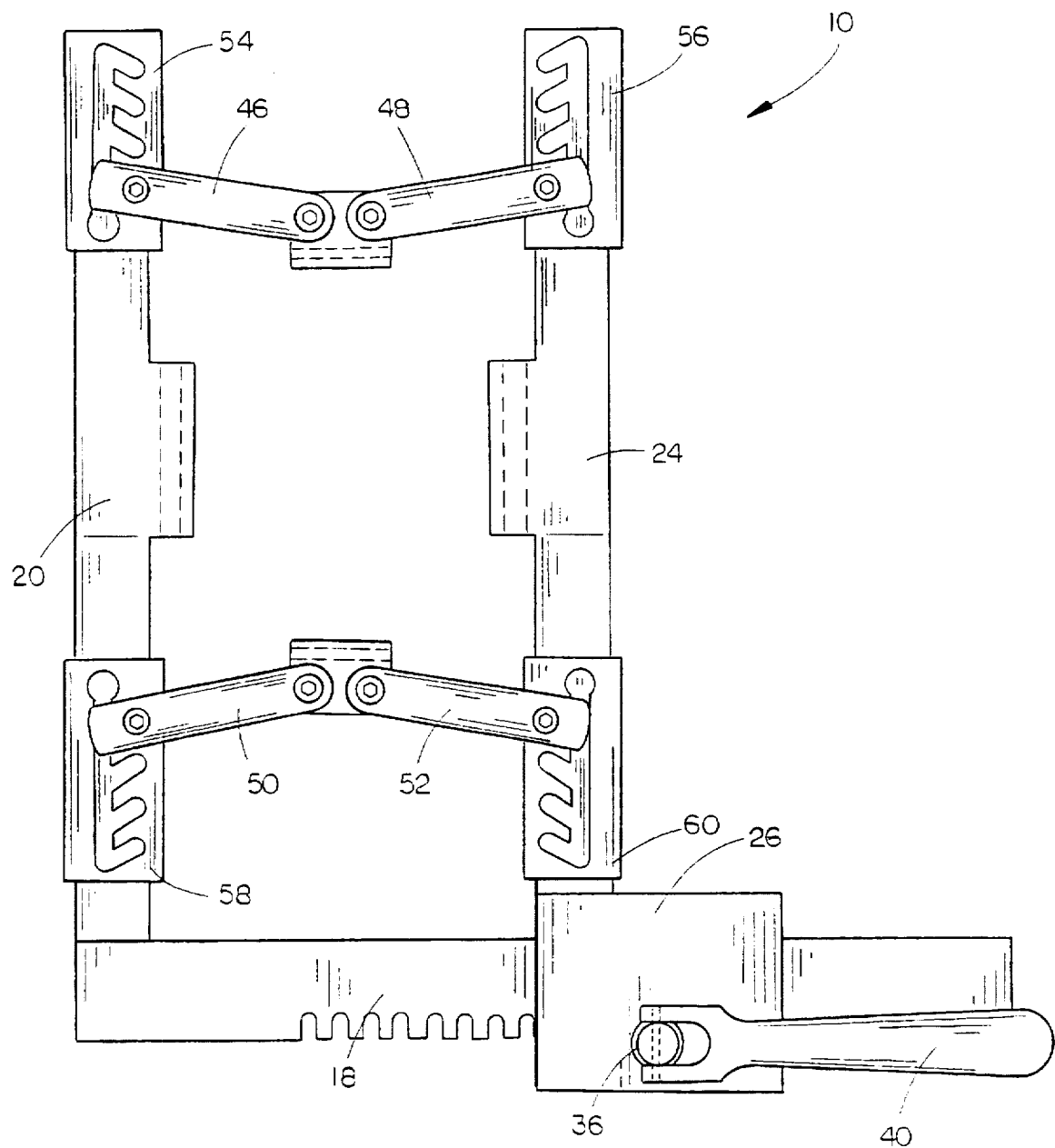
FIG. 5 is a top plan view of the retractor in a fully retracted position.

Referring now to FIGS. 4 and 5, operation of retractor 10 is shown in more detail. FIG. 4 shows retractor 10 in a first position prior to full retraction. Second arm 24 is positioned adjacent first arm 20 such that the first pair of blades 22 and 28 are adjacent one another, and the second pair of blades 42 and 44 are positioned adjacent one another. Links 46 and 48 and links 50 and 52 form a general "V" shape in this initial position.

Movement of blades 22 and 28 away from one another along the Y axis and movement of blades 42 and 44 away from one another along the X axis will occur upon movement of second arm 24 away from first arm 20. Second arm 24 is moved away from first arm 20 by rotating pinion 36 with crank 40 in a counterclockwise direction, to thereby direct rack 34 and move carrier housing 26 towards the rearward end 18b of base leg 18. Thus, a single rotational force on pinion 36 will cause blades 22 and 28 and 42 and 44 to simultaneously move along orthogonal dual axes.

FIG. 5 shows retractor 10 in a substantially retracted position, with arms 20 and 24 spaced apart their maximum distance from each other, and links 46 and 48 nearly coaxial and links 50 and 52 nearly coaxial. In order to provide flexibility in the size of the openings to be retracted, links 46, 48, 50, and 52 are pivotally connected to their associated arms 20 and 24 by connector housings 54, 56, 58, and 60, respectively.

Figure 7:
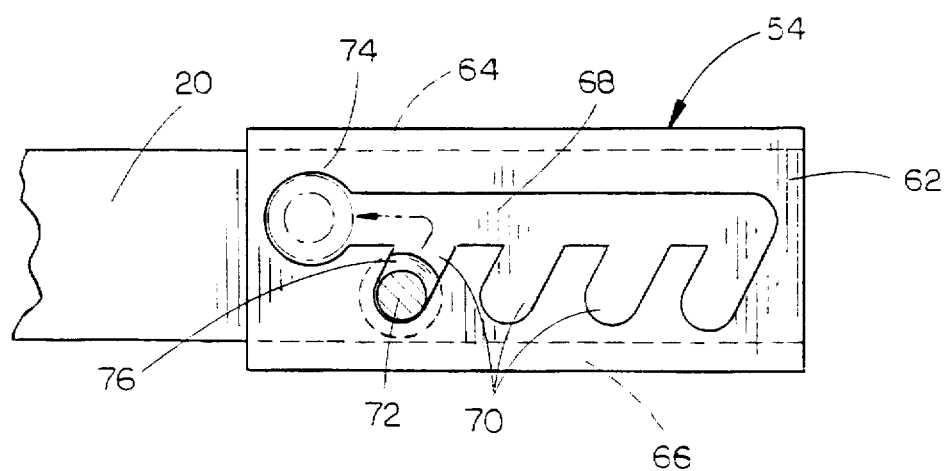
FIG. 7 is an enlarged plan view of one of the link engagement members.

Connector housing 54 is shown in more detail in FIG. 7, and is representative of all four of the connector housings 54, 56, 58 and 60. Connector housing 54 includes a top plate 62 spaced above and parallel to arm 20 by a pair of opposing side walls 64 and 66. An elongated slot 68 extends longitudinally in top leg 62, but less than end to end. A plurality of notches 70 extend transversely from the main slot 68, to form pivot locations for a pivot pin 72 on the associated link. One end of slot 68 has an enlarged opening 74 therein permitting an enlarged head 76 on the depending end of pivot pin 72 to be inserted within slots 68. Head 76 prevents removal of pin 72 from the remainder of slot 68 and notches 70, yet permits slidable and pivotable movement of pin 72.

Referring once again to FIG. 3, it can be seen that the distal ends of links 46, 48, 50 and 52 each have a depending pivot pin 72 thereon, with an enlarged head 76 for slidable and pivotable movement within the respective slots 68 and notches 70 in each of the connector housings 54, 56, 58 and 60. FIG. 4 shows one pair of links 46 and 48 readjusted to a position spaced further away from blade 44, in broken lines. In this way, the distance between blades 42 and 44 may be selectively adjusted prior to the retracting of blades 22, 28, 42, and 44.

Whereas the invention has been shown and described in connection with the preferred embodiment thereof, many modifications, substitutions and additions may be made which are within the intended broad scope of the appended claims.

I claim:

1. A dual axis surgical retractor, comprising:
   a generally L-shaped frame including an elongated longitudinal arm having first and second ends and an elongated base leg rigidly secured to the arm first end and extending transversely therefrom;
   a second elongated arm having first and second ends with means on the first end for operably connecting the arm to the base leg for selective movement towards and away from the first arm along a transverse axis while maintaining the second arm parallel to the first arm;
   a first pair of retractor blades, one blade mounted on the first arm and the second blade mounted on the second arm for movement with the arms along transverse axes;
   a second pair of retractor blades oriented generally orthogonally relative to the first pair of blades, each of said second pair of blades operably connected between the first and second arms by a linkage, for movement towards and away from each other along longitudinal axes in response to movement of the arms towards and away from one another; and
   drive means connected between the second arm and base leg for selectively moving the arms towards and away from one another.

2. The retractor of claim 1, wherein said first pair of blades are mounted on the arms directly opposite one another, to move opposingly along the same transverse axis, and wherein the second pair of blades are mounted on the linkages directly opposite one another, to move opposingly along the same longitudinal axis.

3. The retractor of claim 2, wherein the linkages connecting the second pair of blades to the arms each includes:
   a first link having opposite ends, one end pivotally connected to a blade and the other end pivotally connected to the first arm; and
   a second link having opposite ends, one end pivotally connected to a blade and the other end pivotally connected to the second arm.

4. The retractor of claim 3, wherein said drive means includes a rack formed along the base leg and a rotatable pinion on the second arm in engagement with the rack.

5. The retractor of claim 4, further comprising a crank connected to the pinion for selectively rotating the pinion in clockwise and counterclockwise directions and thereby move all four retractor blades towards and away form each other along orthogonal axes.

6. The retractor of claim 5, wherein each link of the linkages are of equal length.

7. The retractor of claim 6, wherein said linkages are operative to maintain fixed orientation of the second pair of blades throughout the range of movement of the blades.

8. The retractor of claim 7, wherein said linkages further include means for adjustable, pivotally connecting the linkages along a length of the arms.

9. The retractor of claim 8, wherein said means for adjustably, pivotally connecting the linkages to the arms includes:
   a pivot pin proximal the end of each link; and
   an elongated slot formed along a length of each of said arms for slidably, pivotally receiving each pivot pin;
   each slot having a plurality of transverse notches for selectively receiving a pivot pin.

10. The retractor of claim 3, wherein each link of the linkages are of equal length.

11. The retractor of claim 1, wherein the linkages connecting the second pair of blades to the arms each includes:
   a first link having opposite ends, one end pivotally connected to a blade and the other end pivotally connected to the first arm; and
   a second link having opposite ends, one end pivotally connected to a blade and the other end pivotally connected to the second arm.

12. The retractor of claim 1, wherein said drive means includes a rack formed along the base leg and a rotatable pinion on the second arm in engagement with the rack.

13. The retractor of claim 12, further comprising a crank connected to the pinion for selectively rotating the pinion in clockwise and counterclockwise directions and thereby move all four retractor blades towards and away form each other along orthogonal axes.

14. The retractor of claim 1, wherein said linkages are operative to maintain fixed orientation of the second pair of blades throughout the range of movement of the blades.

15. The retractor of claim 1, wherein said linkages further include means for adjustable, pivotally connecting the linkages along a length of the arms.

16. The retractor of claim 15, wherein said means for adjustably, pivotally connecting the linkages to the arms includes:

a pivot pin proximal the end of each link; and an elongated slot formed along a length of each of said arms for slidably, pivotally receiving each pivot pin;

each slot having a plurality of transverse notches for selectively receiving a pivot pin.

17. Apparatus for simultaneously moving two pairs of blades along two independent axes, comprising:

- a generally L-shaped frame including an elongated longitudinal arm having first and second ends and an elongated base leg rigidly secured to the arm first end and extending transversely therefrom;
- a second elongated arm having first and second ends with means on the first end for operably connecting the arm to the base leg for selective movement towards and away from the first arm along a transverse axis;
- a first pair of blades, one blade mounted on the first arm and the second blade mounted on the second arm for movement with the arms along transverse axes;
- a second pair of blades oriented generally orthogonally relative to the first pair of blades, each of said second pair of blades operably connected between the first and second arms by a linkage, for movement towards and away from each other along longitudinal axes in response to movement of the arms towards and away from one another; and
- drive means connected between the second arm and base leg for selectively moving the arms towards and away from one another.

* * * * *